United States Patent [19]

Osten

[11] Patent Number: 5,018,866
[45] Date of Patent: May 28, 1991

[54] METHOD AND APPARATUS FOR PERFORMING HIGH SENSITIVITY FLUORESCENCE MEASUREMENTS

[75] Inventor: Donald E. Osten, Bolingbrook, Ill.

[73] Assignee: Packard Instrument Company, Downers Grove, Ill.

[21] Appl. No.: 405,963

[22] Filed: Sep. 12, 1989

[51] Int. Cl.$^5$ .............................................. G01N 21/64
[52] U.S. Cl. .............................. 356/417; 250/458.1; 250/459.1; 356/318
[58] Field of Search .............. 356/73, 318, 317, 417, 356/440; 250/458.1, 459.1, 461.1

[56] References Cited

U.S. PATENT DOCUMENTS

| | | | |
|---|---|---|---|
| 3,604,927 | 9/1971 | Hirschfeld | 250/71 |
| 3,849,654 | 11/1974 | Malvin | 250/363 |
| 3,939,350 | 2/1976 | Kronick et al. | 250/365 |
| 4,124,302 | 11/1978 | Kuzmin | 356/440 |
| 4,501,970 | 2/1985 | Nelson | 356/318 X |
| 4,802,768 | 2/1989 | Gifford et al. | 356/318 X |

FOREIGN PATENT DOCUMENTS

| | | |
|---|---|---|
| 3447437 | 7/1985 | Fed. Rep. of Germany ........ 356/73 |
| 60-196646 | 10/1985 | Japan . |
| 60-196648 | 10/1985 | Japan . |
| 60-196649 | 10/1985 | Japan . |

OTHER PUBLICATIONS

Schull et al., "Aluminum Ellipse for Decreasing Limits of Defection in Atomic Flourescence Flame Spectrometry", *Analytical Chemistry*, vol. 43, No. 6, May, 1971, pp. 799-800.

*Primary Examiner*—Vincent P. McGraw
*Attorney, Agent, or Firm*—Kareem M. Irfan

[57] ABSTRACT

An improved method and apparatus is provided for performing high sensitivity fluorescence measurements. A liquid sample contained within a cuvette is exposed to exciting radiation in such a way that the radiation is introduced directly to the sample and is restricted from reaching the container walls. The sample container is in the form of a cylindrical cuvette provided with reflector means on the bottom so that any unabsorbed exciting radiation reaching the cuvette bottom is reflected back through the sample solution. Fluorescent radiation emitted by the sample is collected by an ellipsoidal reflector which substantially surrounds the sample container and focuses radiation incident thereupon onto a small area from which it is efficiently sensed by a photodetector. The optical arrangement realizes significantly improved signal-to-noise and signal-to-background ratios.

15 Claims, 3 Drawing Sheets

"PRIOR-ART"

METHOD AND APPARATUS FOR PERFORMING HIGH SENSITIVITY FLUORESCENCE MEASUREMENTS

BACKGROUND OF THE INVENTION

1. Field of the Invention

This invention relates generally to the field of fluorescence spectroscopy. More particularly, this invention relates to an improved technique and apparatus for making fluorescence measurements with increased sensitivity.

2. Description of Related Art

Fluorescence spectroscopy is a widely used technique for performing analytical studies, both quantitative and qualitative, of organic and inorganic materials. Spectroscopic studies of fluorescence characteristics of materials when subjected to radiation of certain wavelengths constitute a convenient means for obtaining information regarding material composition, purity, concentration, turbidity, etc.

In its basic form fluorescence spectroscopy involves the examination of fluorescent radiation resulting from exposing the medium or sample under scrutiny to exciting radiation. In making fluorescence measurements, the sample, which is usually in the form of a solution or a suspension of solid particles in a liquid, is placed within a beam of the desired exciting radiation. The exciting radiation causes the sample to fluoresce and the resulting fluorescence is sensed by a detector and examined. The emitted radiation is usually filtered by some form of secondary wavelength filters or mono- chromators in order to achieve maximum separation of the exciting radiation from the emitted fluorescence, prior to being detected by a photodetector.

Integrity of fluorescence measurements is directly related to the degree to which fluorescent radiation emanating from a sample is isolated from the exciting radiation originally incident upon the sample. Further, the sensitivity of measurement is a function of the extent to which the emitted radiation is actually detected by the photodetector. Achieving these objectives to an optimum extent constitutes a difficult obstacle for conventional fluorescence spectrometry systems and has significantly restricted their operational efficiency.

Problems associated with separation of excited radiation from incident radiation and with detecting a major segment of excited radiation are further compounded when the material or sample under scrutiny is in liquid form. In conventional systems, fluorescence measurements of liquid samples are carried out in standard glass or fused silica cuvettes with exciting radiation or light being focused onto the sample contained within the cuvette through one side of the cuvette. Radiation emitted as the sample fluoresces is measured at right angles to the exciting light.

In such systems, monochromators or interference filters formed of glass or fused silica are used to separate the exciting light from the emission light. This separation is an important aspect of the measurement process and is necessary because the exciting light which is scattered by the sample under scrutiny is typically of much higher intensity than the intensity of the fluorescent emission from the sample. The problem is further compounded by the fact that the photodetectors used for measuring the fluorescent emission generally respond to the exciting wavelengths as well.

Under these conditions, the optics arrangements used with conventional systems for fluorescence measurements are capable of collecting and detecting only a limited amount of emission light from the test cuvette. Since the excitation light is directed into one side of the cuvette while the resulting fluorescence is emitted at equal intensity in all directions, the amount of light which can be gathered is inherently a small fraction of the total amount emitted. Accordingly, the signal-to-noise ratio achievable by conventional fluorescence systems is restricted, thereby restricting the selectivity, efficiency and sensitivity with which fluorescent spectroscopic studies can be made.

Various types of optics arrangements have been used in conventional fluorometry systems in an attempt to improve the efficiency with which fluorescent light emitted from a test sample is collected. Reflective optics have been advantageously used in this regard. As an example, reflective optical components have been employed which surround the conventional glass or fused silica fluorescence cuvettes. Such reflective components surround the cuvette optically and increase coupling of fluorescent emissions to the conventional optics means for collecting emission light. Such arrangements still fall short of being optimum because the reflective optics require transmitting the fluorescent light back through the sample and the cuvette, thereby attenuating the intensity of emitted light considerably.

An additional problem associated with fluorescence measurements in cuvettes results from surface effects which arise regardless of whether the cuvette is composed of glass, fused silica or even plastic. The problem arises because some materials are capable of being selectively adsorbed on the cuvette surfaces. The absorption generates an increase in the fluorescent background level since the exciting light passes through and excites fluorescence from the adsorbed layer prior to reaching the sample solution which is to be excited. In addition, the adsorbed layer also attenuates the intensity of exciting light, thereby reducing the intensity of light available for exciting fluorescence from the sample. The end result is that signal-to-noise and signal-to-background ratios are substantially less than optimum with conventional fluorescence measurement techniques.

SUMMARY OF THE INVENTION

It is a primary object of the present invention to provide an improved method and apparatus for making high sensitivity fluorescence measurements, particularly on liquid samples and the like.

A related object is to provide an improved method and apparatus of the foregoing kind which realizes separation between exciting radiation and resulting fluorescent radiation.

A further object of the present invention is to provide an improved method and apparatus of the above type which is adapted to sensing and detecting a high percentage of fluorescent radiation emitted from the sample under test.

Yet another object of this invention is to provide a high sensitivity method and apparatus for fluorescence measurements which yields high signal-to-noise and signal-to-background ratios during measurements.

The above-enumerated and other objects are achieved, in accordance with the system of this invention, by means of an improved technique for performing fluorescence measurements wherein the sample under test is exposed to exciting radiation or light in such a manner that the exciting light is restricted from reaching the walls of the sample container. Exciting light is introduced into the sample container through the surface of the liquid containing the sample so as to minimize background fluorescence at the point where the light enters the liquid. The exciting light is precisely collimated so that no portion of the light reaches the sample container walls. According to a feature of this invention, the sample container is provided with reflector means on the bottom so that any unabsorbed exciting light which reaches the bottom of the container is reflected back through the sample solution.

Light emitted as the sample fluoresces is collected by a reflector which substantially surrounds the sample. According to another feature of this invention, the reflector is selected to be ellipsoidal in nature so that substantially all of the fluorescent light radiated from the sample region is collected and focused onto a small area from which it may efficiently be sensed by a photodetector.

Since the exciting light contacts only the sample solution and reflector and is prevented from contacting the container walls, secondary fluorescence from the walls is avoided. Significantly improved signal-to-noise and signal-to-background ratios are realized, since the ellipsoidal reflector collects most of the fluorescent light and since sources of background reflections are virtually eliminated.

BRIEF DESCRIPTION OF THE DRAWINGS

Other objects and advantages of the invention will become apparent upon reading the following detailed description and upon reference to the drawings in which.

Figure 1:
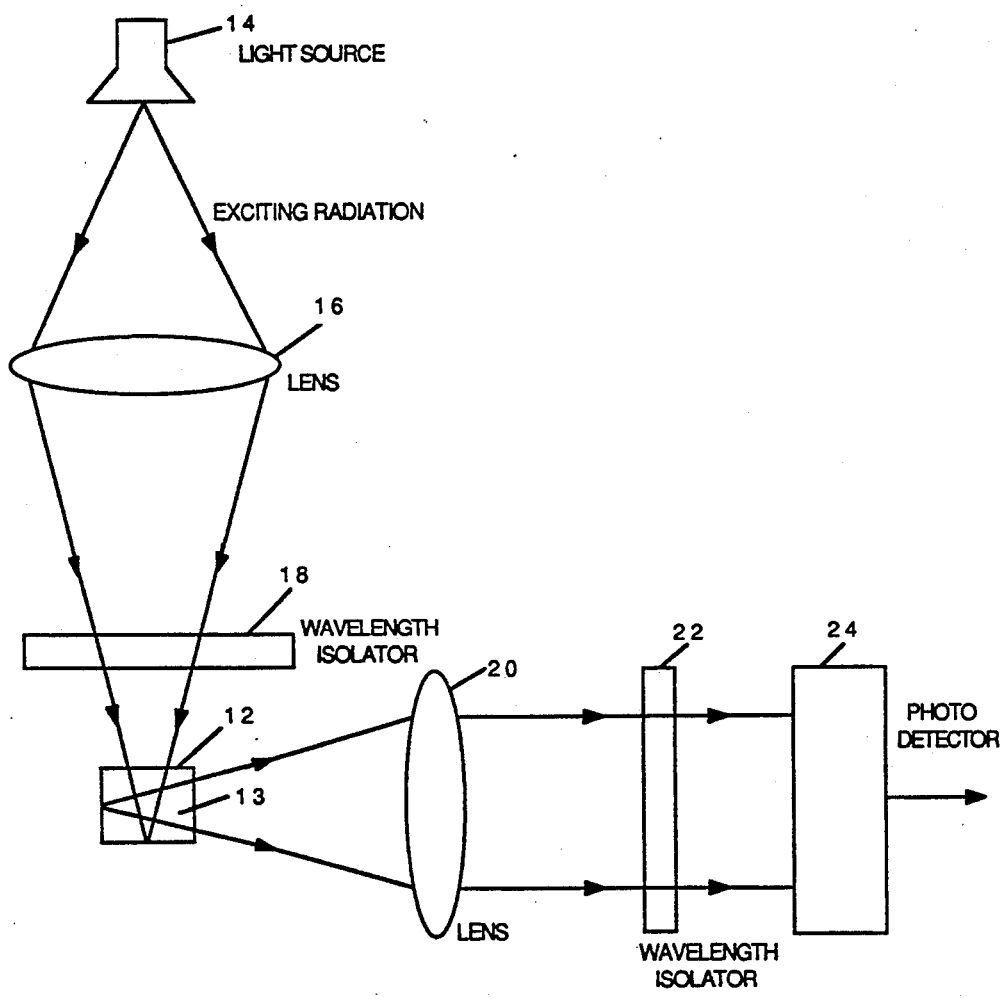
FIG. 1 is schematic illustration of a conventionally used apparatus and method for performing fluorescence measurements.

While the invention is susceptible to various modifications and alternative forms, specific embodiments thereof have been shown by way of example in the drawings and will herein be described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

DESCRIPTION OF THE PREFERRED EMBODIMENTS

Referring now to FIG. 1, there is shown a schematic illustration of apparatus conventionally used for performing fluorescence measurements. As shown, in conventional apparatus, generally designated as 10, the sample 12 to be monitored is carried within a standard cuvette 13 which is typically formed of glass or fused silica. Exciting radiation from a light source 14 passes through an optical lens 16 and is focused onto the sample 12 after being directed through some type of wavelength isolation device 18 which functions to allow only light of a desired wavelength to pass through. The exciting light is brought into one side of the cuvette and the resulting fluorescent radiation is measured at right angles to the direction of incidence of the exciting light.

As shown in FIG. 1, the system detects fluorescent radiation emanating from the side of the cuvette immediately adjacent to the side on which the exciting radiation is incident. Such radiation is focused through an optical lens 20 and passed through a wavelength isolation device 22 onto a photodetector 24. The output of photodetector 24 is representative of the fluorescent radiation captured by the optical lens 20.

In the above arrangement, fluorescence only occurs when the wavelength of the exciting light is shorter than the wavelength of emitted light. The wavelength isolation device 22 is in the form of a monochromator or an interference filter composed of glass or fused silica and functions to separate the exciting light from the emitted light. This separation is essential because the photodetector 24 conventionally used for measuring the fluorescent emission typically responds to the wavelength of the exciting light also and because the exciting light which is scattered by the sample following incidence thereupon can possess an intensity which is much higher than that of the fluorescent emission.

A major problem with the above type of conventional apparatus is that only a small fraction of the total amount of light emanating from the cuvette is detected. This is because, although the exciting light is directed only into one side of the cuvette, the resulting fluorescent radiation is emitted at equal intensity in all directions. A further problem associated with such side-wise fluorescence measurements on liquid samples in cuvettes arises from the fact that certain materials may be selectively adsorbed on these surfaces. Since the exciting light passes through and excites fluorescent radiation from the adsorbed layer prior to reaching the sample itself, the fluorescent background level is increased. In addition, the adsorbed layer also brings about an attenuation in the intensity of the exciting light, thereby reducing the intensity of light which remains available for exciting fluorescence from the sample. As a result of the foregoing problems, signal-to-noise and signal-to-background ratios associated with conventional fluorescence measurement apparatus are restricted to less than optimum levels.

Figure 2:
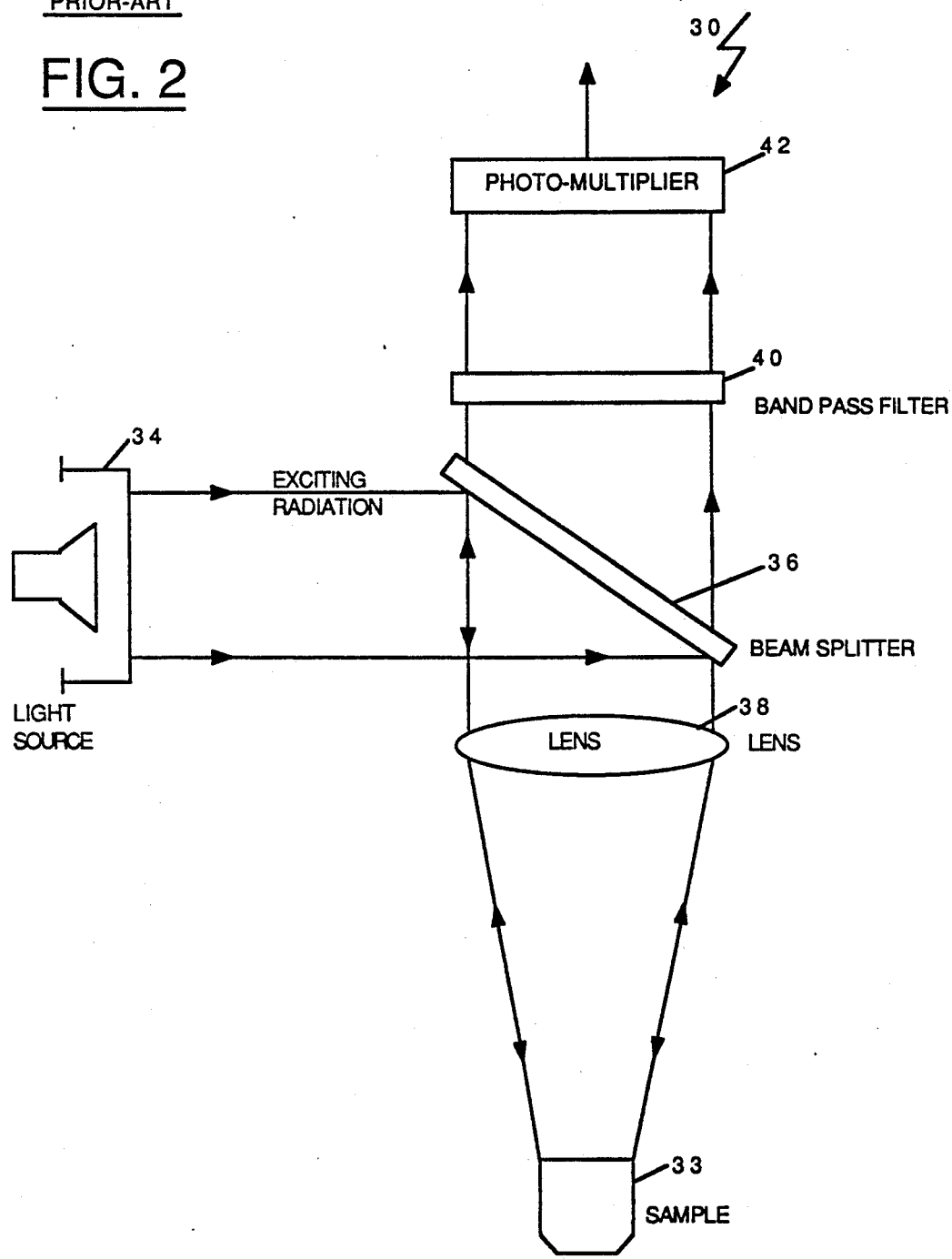
FIG. 2 is schematic illustration of another conventional arrangement using a beam splitter to direct and separate exciting light and fluorescent light.

Referring now to FIG. 2, there is shown another conventional apparatus 30 for fluorescence measurements which overcomes some of the foregoing problems associated with the apparatus of FIG. 1. As shown therein, the sample 32 is exposed to exciting radiation which is generated by a light source 34 and is introduced into the sample container 33 through the surface of the liquid, rather than through the side walls of the container. More specifically, the exciting radiation is in the form of collimated light and is focused onto a beam splitter 36 which reflects incident light downwardly to an optical lens 38 which focuses the incident light directly onto the sample 32.

The beam splitter 36 is typically a dichroic filter which exhibits a high reflectivity (of the order of 99%) for the exciting light. The filter is positioned in such a way that the exciting light is reflected directly downwardly thereof. Fluorescent radiation or light emitted by the sample 32 is collimated by the optical lens 38 and becomes incident back on the dichroic filter 36. The filter possesses a high transmission characteristic (of the order of 95%) for light having a wavelength longer than that of the exciting light. Since the wavelength of the fluorescent emission is longer than that of the exciting light, virtually all of the fluorescent light incident on the beam splitter 36 passes through. Such light is passed through a bandpass filter 40 where it is filtered down to a desired wavelength and is subsequently detected by a photo-multiplier unit 42 whose output serves as a measure of fluorescence emitted from the sample 32.

The above arrangement reduces background fluorescence at the point of entry of exciting light since the light is introduced into the sample through the surface of the liquid rather than through the container side walls. Surface adsorption problems, as well as problems with fluorescence of the sample container, are reduced to some extent since both the exciting light and the fluorescent light follow a substantially common path. However, a major problem remains in that the efficiency with which fluorescent radiation emitted by the sample is collected is not optimum. In addition, it is possible for surface fluorescence to be excited by the unabsorbed portion of the exciting beam of light which strikes the bottom of the sample container. In the arrangement of FIG. 2, it is also possible for a high background fluorescence level to exist because of fluorescence from the lens and the dichroic filter which are used in the path of the exciting light and the emission light.

Figure 3:
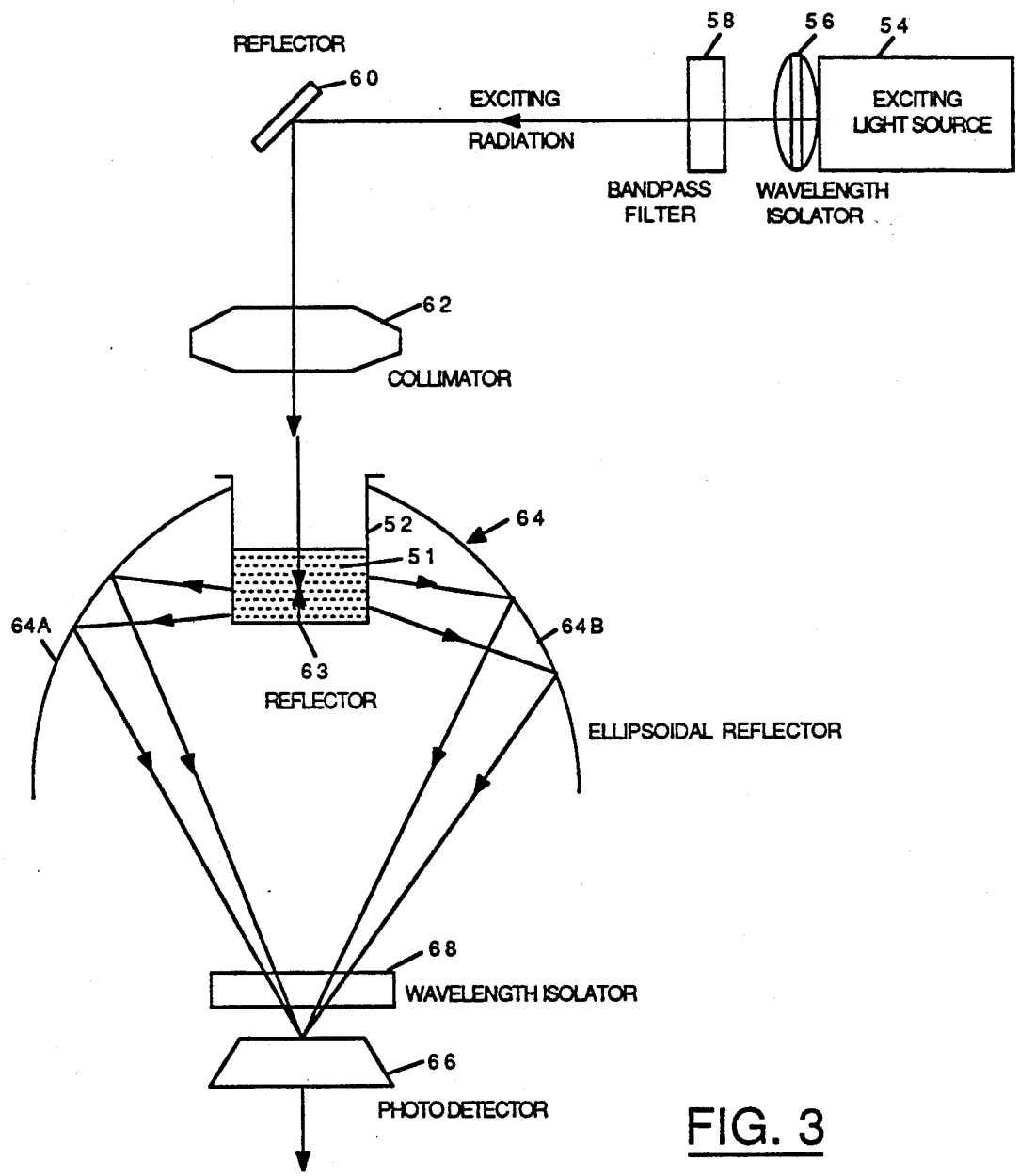
FIG. 3 is a schematic illustration of an exemplary arrangement for making improved fluorescence measurements and embodying the principles of the present invention.

Turning now to FIG. 3, a schematic illustration is presented of an optical arrangement which overcomes the above-discussed problems associated with conventional fluorescence measurement apparatus. According to a preferred embodiment of this invention, FIG. 3 shows a fluorescence measurement arrangement 50 wherein a liquid sample 51 contained within a sample container 52 is exposed to exciting light from a light source 54 such as a lamp, laser or flash lamp. Preferably, the output of light source 54 is passed through a wavelength isolator 56 which is in the form of an interference filter composed of glass or like material or a spectrometer and is adapted to isolate light of a desired wavelength. The output of wavelength isolator 56 is passed through a bandpass filter 58 which further restricts the incident light to within a desired frequency band. Subsequently, the exciting light is focused onto a 45 reflector arrangement 60 which reflects incident light downwardly into the sample container 52. Alternatively, the exciting light may directly be introduced into the container without any reflector arrangement.

The sample container 52 is preferably in the form of a substantially cylindrical cuvette which is composed of glass, fused silica, synthetic plastic or like material which is permeable to fluorescent radiation from the sample. According to a feature of this invention, the exciting light is precisely collimated through a collimator 62 in such a way that the light is introduced directly onto the liquid sample through the open side of the sample container 52 without reaching any of the side walls of the container. Preferably, the light is focused on the sample substantially about the central section of the open side of the container.

According to an important feature of this invention, the bottom surface of the sample container 52, which may be flat or curved, is provided with reflector means 63 in the form of a coating of material which presents total reflectance to any exciting light incident thereupon. Any portion of the incident exciting light which passes through the liquid sample without being absorbed and which subsequently strikes the bottom of the sample container 52 is reflected straight back through the sample solution without being scattered randomly through the sample solution to the container walls.

As a result, the length of the absorption path through the liquid sample is effectively doubled since the sample is subjected to the fluorescing effects of the exciting light both during the incidence path (as the exciting light enters the liquid sample and passes through it to the bottom of the sample container) and the reflected path (as unabsorbed exciting light is reflected from the container bottom upwardly through the liquid sample). A major advantage of this arrangement is that the destructive effects of fluorescence from the container walls, as prevalent in conventional fluorescence measurement systems, are awarded since the exciting light contacts only the sample solution and the reflector and is prevented from contacting the container walls.

According to another important feature of this invention, fluorescent radiation which is emitted from the liquid sample in all directions is collected by means of a reflector 64 which effectively surrounds the sample container 52. Preferably, the reflector 64 is an ellipsoidal reflector disposed about the sample container 52 in such a manner that the major axis of the reflector is substantially aligned with the beam of exciting light which is incident on the liquid sample. In addition, the elliptical surfaces 64A, 64B of the reflector 64 extend downwardly of the walls of the sample container 52. In effect, the reflector 64 is adapted to accept substantially all of the fluorescent radiation emanating from the liquid sample.

The fluorescent radiation which is incident on the reflector is focused downwardly therefrom onto a small area defined about the focal point "F" of the reflector. A photodetector 66 is positioned about the focal point "F" and is adapted to sense and detect all the fluorescent radiation at that point. Preferably, the focused fluorescent light is passed through a wavelength isolator 68 prior to detection so that only light of a desired range of wavelength is detected. In the above arrangement, most of the fluorescent light emitted from the sample is collected and focused by the ellipsoidal reflector 64; thus, the output of photodetector 66 represents an accurate measure of the degree of fluorescence induced within the sample by the exciting radiation.

The use of the ellipsoidal reflector permits the capture of all the radiation emitted from the sample region. Further, all such radiation is focused onto a small region about the focal point of the reflector. This permits increased signal throughput for the photodetector which can directly measure the focused light. If, instead, a paraboloidal reflector were to be used, the fluorescent radiation incident on the reflector would be collimated, thereby requiring the subsequent use of an optical lens to scale the collected fluorescent beam down to the image size to which conventional photodetectors are capable of responding. The ellipsoidal reflector obviates the need for the additional optical components since it effectively combines the collimation and focusing operations.

In effect, the novel optical arrangement according to the system of this invention eliminates secondary fluorescence from the container walls and also eliminates the effects of surface adsorption, thereby substantially reducing the background fluorescence level and permitting improved discrimination between exciting light and emitted radiation light. Further, measurement of low intensity fluorescent samples becomes possible with a high degree of sensitivity since virtually all fluorescent radiation emitted from the sample material is collected and detected.

The above-described advantages of the present invention have been confirmed in practice by experimental fluorescence measurements which reveal up to a tri-fold increase in measurement sensitivity, as indicated by the signal-to-background ratio, by using the optical arrangement of FIG. 3 as compared to the conventional arrangement of FIG. 2, under identical conditions of sample concentration, light intensity and wavelength, etc.

I claim:

1. A method of performing fluorescence measurements on a sample capable of being activated by exciting radiation, said method comprising the steps of:
   enclosing the sample within a container having surrounding walls and an open side facing a bottom surface, said bottom surface having reflector means for reflecting any radiation incident thereupon;
   introducing a beam of exciting radiation through said open side of container directly onto the sample contained therein in a direction normal to said reflector surface in such a way that said beam does not reach said container walls, thereby avoiding any secondary fluorescence therefrom, any portion of said beam which is unabsorbed by the sample and traverses through the sample to strike said reflector means on said bottom surface being reflected therefrom back through the sample without reaching said container walls, thereby avoiding any secondary fluorescence therefrom;
   collecting fluorescent radiation from the sample through collector means surrounding said container walls, said collector means being adapted to focus said fluorescent radiation incident thereupon onto a predefined area; and
   detecting and measuring said fluorescent radiation focused onto said predefined area.

2. The method of making fluorescence measurements as set forth in claim 1 wherein said container is in the form of a cuvette formed of glass, quartz, synthetic plastic or like material which is permeable to said fluorescent radiation.

3. The method of making fluorescence measurements as set forth in claim 2 wherein said cuvette is substantially cylindrical, and wherein the walls and bottom surface thereof, in combination, define a cavity for receiving a fluid sample.

4. The method of making fluorescence measurements as set forth in claim 1 wherein said exciting radiation is collimated so as to be focused on the sample through said open side of said sample container without reaching said container walls.

5. The method of making fluorescence measurements as set forth in claim 1 wherein said exciting radiation is filtered to a desired range of wavelength prior to being focused onto the sample.

6. The method of making fluorescence measurements as set forth in claim 1 wherein said collector means is in the form of an ellipsoidal reflector surrounding said container walls, said reflector being disposed with its major axis aligned substantially with said beam of exciting radiation incident on the sample, whereby fluorescent radiation emanating from the sample in all directions is collected and reflected so as to be focused substantially about the focal point of said ellipsoidal reflector.

7. The method of making fluorescence measurements as set forth in claim 6 wherein said focused fluorescent radiation is filtered to a desired wavelength and detected by a photodetector positioned about said focal point of said reflector.

8. Apparatus for performing fluorescence measurements on a sample by detecting fluorescence induced in the sample by focusing exciting radiation thereupon, said apparatus comprising:
   a sample container having surrounding walls and an open side facing a bottom surface, said walls and bottom surface defining a sample-containing cavity, said bottom surface being provided with reflector means for reflecting any radiation incident thereupon;
   means for introducing a beam of exciting radiation through said open side of container directly onto the sample contained therein in a direction normal to said reflector surface in such a way that said beam does not reach said container walls, thereby avoiding any secondary fluorescence therefrom, any portion of said beam which is unabsorbed by the sample and traverses through the sample to strike said reflector means on said bottom surface being reflected therefrom back through the sample without reaching said container walls, thereby avoiding any secondary fluorescence therefrom;
   collector means for collecting fluorescent radiation emitted from the sample, said collector means substantially surrounding said container walls and being adapted to focus said fluorescent radiation incident thereupon onto a predefined area; and
   means for detecting said focused fluorescent radiation.

9. The apparatus for making fluorescence measurements as set forth in claim 8 wherein said sample container is in the form of a cuvette formed of glass, quartz, synthetic plastic or like material which is permeable to said fluorescent radiation.

10. The apparatus for making fluorescence measurements as set forth in claim 9 wherein said cuvette is substantially cylindrical, and wherein the walls and bottom surface thereof, in combination, define a cylindrical cavity for receiving a fluid sample.

11. The method of making fluorescence measurements as set forth in claim 8 further including means for collimating said exciting radiation so as to be focused on the sample substantially about the central section of said open side of said sample container without reaching said container walls.

12. The apparatus for making fluorescence measurements as set forth in claim 8 further including means for filtering said exciting radiation to a desired wavelength prior to being focused onto the sample.

13. The apparatus for making fluorescence measurements as set forth in claim 8 wherein said collector means is in the form of an ellipsoidal reflector surrounding said container walls, said reflector being disposed with its major axis aligned substantially with s id beam of exciting radiation incident on the sample, whereby fluorescent radiation emanating from the sample in all directions is collected and reflected so as to be focused substantially about the focal point of said ellipsoidal reflector.

14. The apparatus for making fluorescence measurements as set forth in claim 13 further including means for filtering said focused fluorescent radiation to a desired range of wavelength.

15. The apparatus for making fluorescence measurements as set forth in claim 14 wherein said means for detecting said focused fluorescent radiation comprises a photodetector positioned about said focal point of said reflector.

* * * * *